United States Patent
Corona

[11] Patent Number: 5,189,735
[45] Date of Patent: Mar. 2, 1993

[54] WELDING SYSTEM WITH AUTOMATIC WELDING HELMET AND SAFETY CIRCUIT

[76] Inventor: Peter J. Corona, 1130 W. Marine, Apt. 21, Gardena, Calif. 90247

[21] Appl. No.: 671,503
[22] Filed: Mar. 19, 1991
[51] Int. Cl.⁵ .......................... A42B 1/00; A61F 9/00
[52] U.S. Cl. ......................................... 2/8; 219/147
[58] Field of Search ................... 2/8, 9, 424; 219/147

[56] References Cited

U.S. PATENT DOCUMENTS

| | | | |
|---|---|---|---|
| 2,678,369 | 5/1954 | Van Hook | 219/147 |
| 2,761,046 | 8/1956 | Herrick et al. | 219/147 |
| 2,904,669 | 9/1959 | Toebe | 219/147 |
| 3,096,430 | 7/1963 | Farr | 2/8 |
| 3,719,793 | 3/1973 | Finger | 219/147 |
| 3,792,226 | 2/1974 | Bush | 219/147 |
| 3,838,247 | 9/1974 | Finger et al. | 2/8 |
| 3,873,804 | 3/1975 | Gordon | 219/147 |
| 4,011,594 | 3/1977 | Guilbaud et al. | 2/8 |
| 4,101,979 | 7/1978 | Tarrone | 2/8 |
| 4,293,757 | 10/1981 | Niemi | 2/8 |
| 4,638,146 | 1/1987 | Koyama | 219/147 |
| 4,694,141 | 9/1987 | Hahn | 219/147 |
| 4,937,879 | 7/1990 | Hall et al. | 219/147 |

FOREIGN PATENT DOCUMENTS 2040118  8/1980  United Kingdom ............... 2/8

Primary Examiner—Andrew M. Falik
Assistant Examiner—Michael A. Neas
Attorney, Agent, or Firm—Christie, Parker & Hale

[57] ABSTRACT

A welding system with an automatically operated helmet closes the helmet's hood, and thus its face mask, before turning on a welding electrode. The system includes an actuator with a piston that mount to the helmet's headband and hood, respectively. Only when the system detects that the mask is closed will power to the electrode be actuated. This system is controlled by a safety circuit, which the welder simply plugs the helmet into for automatic control. If the welder does not plug into the safety circuit, the system operates similar to a conventional welding system.

7 Claims, 4 Drawing Sheets

5,189,735

WELDING SYSTEM WITH AUTOMATIC WELDING HELMET AND SAFETY CIRCUIT

BACKGROUND OF THE INVENTION

1. Field of the Invention

This invention relates to electric arc welding apparatus and, more particularly, to a system in which a welding helmet automatically rotates down before an arc is struck.

2. Description of the Art

In the technology or electric arc welding, there are primarily three types of systems: (a) a consumable metal rod coated with a solid flux; (b) tungsten inert gas (TIG); and (C) consumable metal inert gas (MIG). As in all electric arc welding systems, the welder must, before any welding can be done, strike an arc so that the necessary heat is formed to meld the work metal and the welding rod. In order to provide an aesthetic, strong weld, the arc must be formed as close as possible to the area where the weld is needed; otherwise, the heat from the arc will meld and weaken the body of the work. As the welder cannot see the work whenever an ultraviolet face shield of the helmet covers his face, the welder must strike the arc as quickly as possible after covering his face to avoid inadvertently moving the welding rod.

If the welder strikes the arc before he covers himself, he can accurately position the arc, but this invites physical and eye damage. The preferred technique is to bring the tip of the welding rod as close to the work area as possible while the helmet is in its raised position and quickly let the helmet fall just before the arc is struck. This takes tremendous skill on the part of the welder because, if the helmet drops too fast, the welder's reflexes cause the tip of the welding rod to jump, and if the helmet is dropping too slowly, the welder's hand will have a strong tendency to wander.

U.S. Pat. No. 4,937,879 (to Hall et al) teaches one solution to this problem. This patent discloses a helmet face shield actuator cylinder attached to the face piece of the helmet, and the piston is attached to the stationary headband. Although this patent teaches automatically lowering the face piece and preventing the formation of the arc until after the face piece is in place, extra weight is added to the moving face piece, making the welder less than comfortable. In addition, different helmet designs require a specially designed actuating means, and Hall et al use a relatively complex circuit for controlling movement of the face piece and striking of the arc.

SUMMARY OF THE INVENTION

The present invention is a welding system With a remote switch control that first turns on an automatic face mask lowering device of a welding helmet. Once the mask is lowered, the welding system automatically turns on a welding electrode or rod.

In one embodiment, the welding system includes a welding control circuit, a remote control for the circuit, a welding helmet having a hood with a face mask, an automatic hood lowering device, a safety circuit to turn on the automatic lowering device in response to operation of the remote control before turning on a welding electrode, and a detector to detect when the hood is lowered. The safety circuit then turns on the welding electrode in response to detection of the lowered hood.

DETAILED DESCRIPTION OF THE PREFERRED EMBODIMENT

Figure 1:
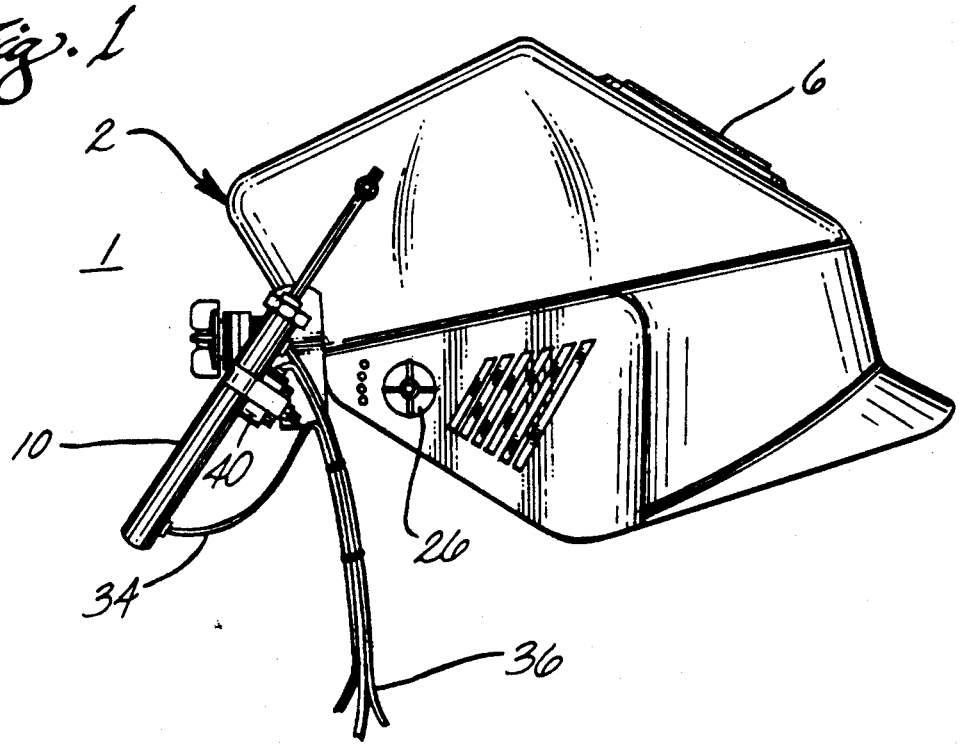
FIG. 1 is a side view of a welding helmet in accordance with the invention with the hood in a raised position.
Figure 2:
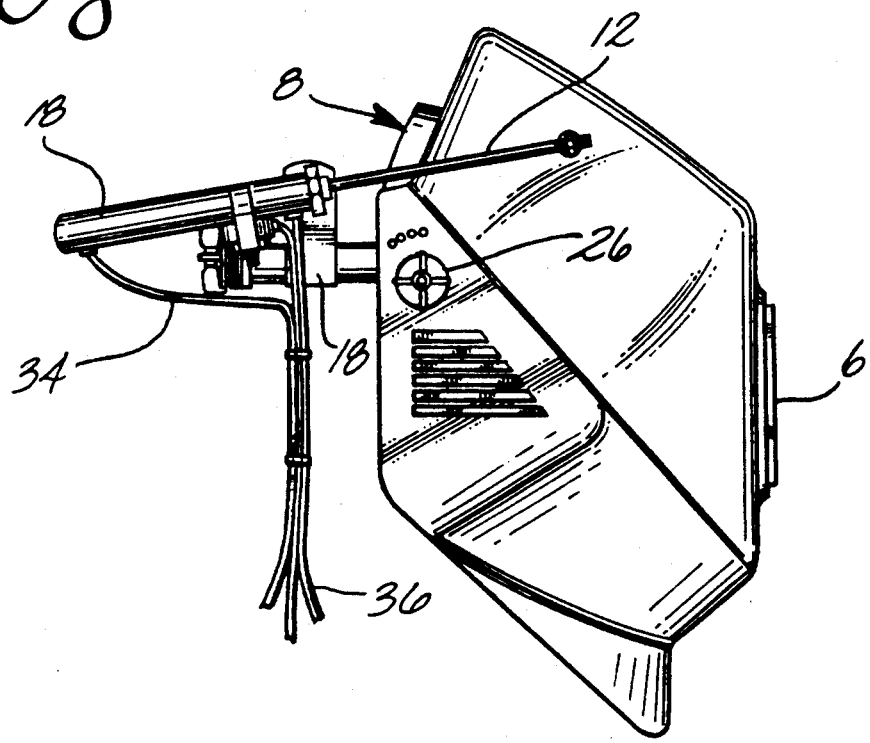
FIG. 2 is a side view of the helmet of FIG. 1 with the hood in a lowered position.
Figure 3:
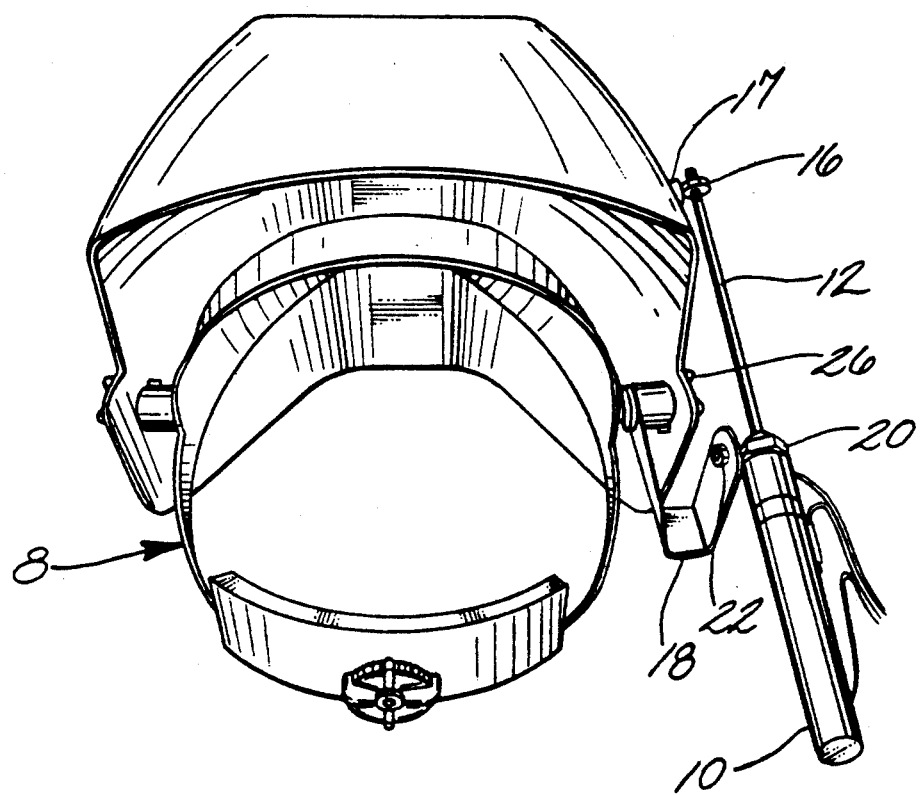
FIG. 3 is a rear view of the helmet of FIG. 2.

With reference to FIGS. 1-3, a welding system according to the invention includes a welding helmet 1 with a hood 2 with a face mask 6 mounted thereon, and an adjustable headband 8 on which the hood 2 rotatably mounts. An automatic face mask (hood) lowering and raising device mounts on the helmet at two points to automatically lower and raise the hood 2 when a person is wearing the helmet. The device includes an air cylinder 10 having a piston 12. A distal end of the piston 12 is fixed to the hood by a banjo nut 16 threaded to a nut (not shown) via a hole in the hood 2. A nylon bushing 17 provides clearance between the hood surface and cylinder mounting, described below.

The cylinder 10 attaches to a bracket 18 by means of another banjo nut 20 threaded to a nut 22. The bracket 18 is shaped to provide clearance between itself and the hood, and between the hood and piston.

Figure 4:
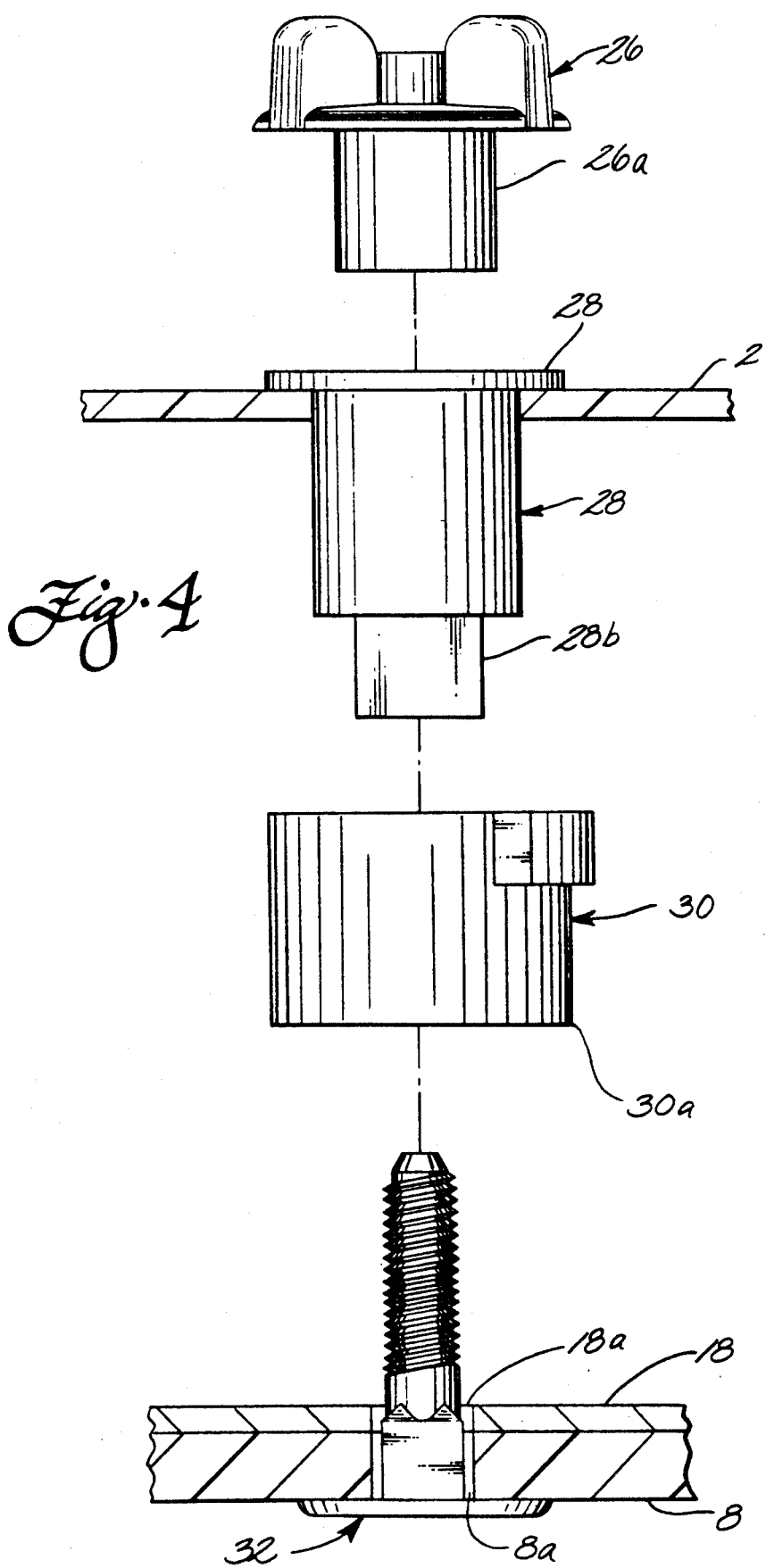
FIG. 4 is an enlarged, exploded view of a portion of the helmet of FIG. 1 for fastening the hood to a headband of the helmet.

The rotatable attachment of the band and hood is shown best in full in FIG. 3 and in detail in FIG. 4. A plastic bolt 26 has an internally threaded cylindrical extension 26a, which sits inside a plastic bushing 28 The bushing 28 has a shoulder 28a that meets the hood 2. Bushing 28 has a square end 28b projecting from its cylindrical body. The bushing sits in a plastic cylindrical receptacle 30, with an end 30a that is closed except for a square hole sized to pass square end 28b. The receptacle seats on bracket 18 which, in turn, abuts band 8. A plastic screw 32 threads inside extension 26a, square end 28b, and extends into square holes 18a, 8a of bracket 18 and band 8, respectively. The hood 2 mounts to the other side of band 8 in the same way, but without bracket 18. With this construction, the hood rotates clockwise about bushing 28 when piston 12 extends to lower the hood, and thus mask 6, into the position of FIG. 2, and counterclockwise when piston 12 retracts to raise the hood, and thus mask 6, to the position of FIG. 1. To extend the piston, air enters the cylinder via inlet tube 34. To retract the piston, air exits via outlet tube 36.

In accordance with one aspect of the invention, the actuator 10 mounts to the headband through the bracket 18, and the piston attaches to the hood to reduce the weight of the hood which must be lowered and raised. In addition, the bracket 18, banjo nuts 16, 20, nylon bushing 17, and actuator 10 and piston are sized and positioned to virtually universally fit all helmet types. Thus, the system can readily be sold as a kit, e.g., with templates to determine where to position the banjo nut 16, depending on the helmet's shape.

Figure 5:
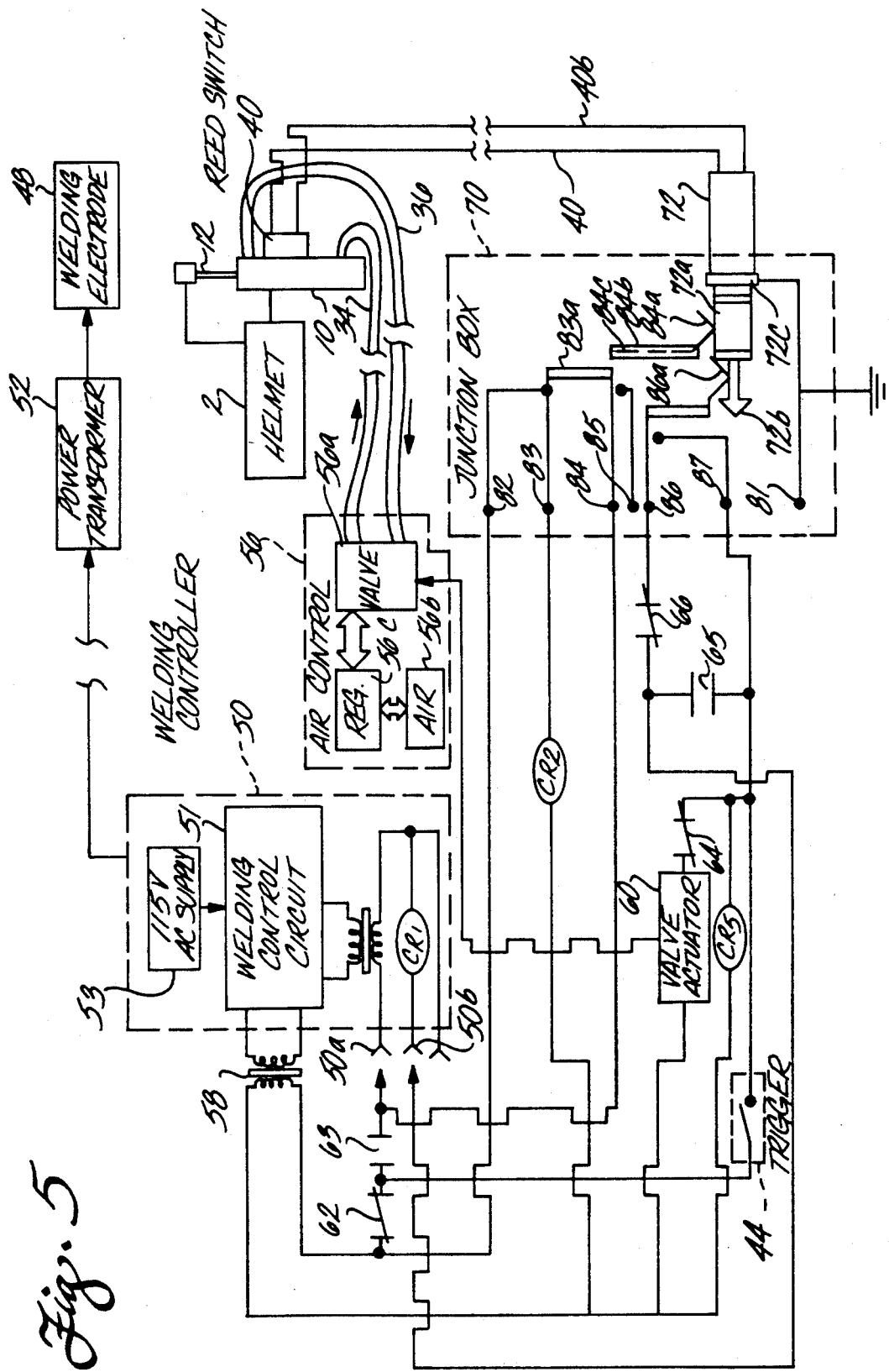
FIG. 5 is a schematic view of the welding control and safety system according to the invention.

In accordance with another aspect of the invention, turning on and off of the welding electrode or rod is controlled in relation to extension and retraction of piston 12 by a safety circuit connected to a magnetic reed switch 40 mounted to the cylinder 10 and to a (foot- or hand-actuated) remote control trigger 44. The trigger turns on a welding controller which actuates a welding electrode or rod 48, as shown in FIG. 5.

In general, the system works as follows: A conventional welding controller 50, except for modifications explained below, when actuated, drives a conventional power transformer 52 to turn on an arc welding electrode or rod 48, such as in MIG or TIG welding. Pressing the trigger 44, in a conventional system, would cause the welding controller 50 to drive the power transformer 52 and actuate electrode 48. However, in the system according to the invention, first, an air control device 56 is actuated to supply air to the cylinder 10 to rotate the helmet down. Then, the reed switch 40 closes when the helmet is down, to close the safety circuit and actuate the welding controller 50.

In more detail, the safety circuit connects to the welding controller in two places. First, at a transformer 51a of a welding control circuit 51 and, second, at a transformer 58 connected to an AC power supply 53 via circuit 51. The transformer 51a is generally known in the art, but, in the invention, it is preferably a step-down transformer from 115 V to 24 V. Transformer 58 is also preferably a step-down transformer, from 115 V to 24 V.

The safety circuit connects these transformers with the following elements: trigger 44; a valve actuator 60 for controlling air control device 56; two relay controls CR2, CR3; relays 62, 63, 64, 65, 66; and a junction box 70. Box 70 receives a stereo plug 72 connected to wires 40a, 40b which meet at normally open reed switch 40. Contact 71a of plug 72 connects to wire 40a; contact 72b connects to wire 40b; and contact 72c leads to ground.

The junction box 70 has seven junction points 81-87. Movable contact arm 84a connects to contact 72a, and movable contact arm 86a connects to contact 72b of plug 72, when the plug is inserted into box 70. This lifts arm 84a out of contact with terminal 85 and into contact with terminals 82, 83. Arm 86a is lifted out of contact with terminal 87.

When plug 72 is not inserted, relays 63 and 65, which are controlled by CR2, are normally closed so that if trigger 44 is closed, the welding controller is actuated via receptacles 50a, 50b. (Control relay CR1 operates relays inside the welding control circuit 51 of controller 50 to turn on the welding electrode 48.) Relays 62, 64, controlled by CR2, and relay 66, controlled by CR3, are normally open. Thus, closing trigger 44 causes current to flow through relay 63, through trigger 44, through relay 65, through receptacle 50b, through CR1, past the secondary winding of transformer 51a, and to receptacle 50a.

When the plug 72 is in, the safety circuit will operate. Terminals 82 and 83 are connected, and terminal 84 is connected, as shown, and terminals 86 and 87 are disconnected. Closing trigger 44 first causes current to flow from the secondary winding of transformer 58 through terminals 82, 83 and CR2 to close relays 62, 64 and open relays 63, 65. Since relay 63 is open, the transformer 51a is isolated so CR1 cannot be operated to turn on the welding control circuit 51.

It should be noted that elements 83a and 84b are insulating push rods, with wire 84c connecting terminal 84 and contact arm 84a. Push rod 83a does not contain a wire.

Closing relay 64 operates valve actuator 60 to move a solenoid valve 56a in air control 56 to a position to let air from an air supply 56b pass through, via regulator 56c, to tube 34 to extend piston 12.

CR3 is also operated to close relay 66. However, since magnetic reed switch 40 is normally open, the portion of the circuit connecting through the transformer 51a remains open. When piston 12 extends to the point where the mask is lowered, switch 40 closes, thus closing the circuit to transformer 51a, using terminals 84, 86 and wires 40a, 40b. This turns on the welding control circuit 51. When the trigger 44 is released, the relays 62, 63, 64, 65, 66 return to the states they were in prior to closing the trigger, and power to the welding electrode is halted. The valve actuator 60 thus releases the solenoid valve 56a, allowing air to exit from cylinder 10 via tube 36 to retract piston 12 and open the helmet.

The above embodiment is exemplary. The invention is thus defined by the claims and not limited to the disclosed embodiment.

I claim:

1. A welding system comprising:
   a helmet comprising a headband harness, a hood having an arc welding face mask attached thereto, and means for pivotably attaching the hood to the headband;
   actuating means mounted to the harness and hood for movement between a first and second position to pivot the hood between upper and lower positions, respectively;
   means for controlling the actuating means;
   means for detecting whether the actuating means is in the first or second position;
   an arc welding electrode;
   a welding controller for turning on and off the electrode;
   a trigger actuable for actuating the welding controller; and
   a safety circuit for connecting the trigger, detecting means, means for controlling the actuating means and the welding controller such that the actuating means moves the hood to the lower position prior to the actuation of the welding controller, wherein the welding controller comprises a first transformer and the safety circuit comprises a second transformer connected to the welding controller, the first and second transformers being connected in series to the trigger along partly overlapping first and second electrically conductive paths, respectively, the safety circuit further comprising a normally open switch disposed along the first path and responsive to the actuating means for closing when the actuating means is in the second position to thereby enable welding when the hood is in the lower position and for opening when the actuating means is not in the second position to thereby disable welding when the hood is not in the lower position, and wherein the safety circuit further comprises means for rendering the second path conductive in response to pressing the trigger, the means for controlling the actuating means being responsive to current flow along the second path.

2. The system of claim 2 wherein the actuating means comprises an air cylinder mounted to the headband through a bracket and a piston mounted to the hood at a position remote from the air cylinder.

3. The system of claim 2 wherein the first and second transformers are step-down transformers to 24 volts.

4. A welding system comprising:
a helmet comprising a headband harness, a hood having an arc welding face mask attached thereto, and means for pivotably attaching the hood to the headband;
actuating means mounted to the harness and hood for movement between a first and second position to pivot the hood between upper and lower positions, respectively;
means for controlling the actuating means;
an arc welding electrode;
a welding controller including a first relay control for turning on and off the electrode;
a trigger actuable for actuating the welding controller; and
a safety circuit having first, second, and third electrical flow paths with respective relays and a normally open switch for closing when the actuating means is in the second position to thereby close the first flow path, the first flow path connecting the welding controller with the trigger and the normally open switch, the second flow path connecting the trigger with the means for controlling, the third flow path having a second relay control, wherein a third relay control is disposed along the second flow path, wherein the third flow path is normally closed, and wherein in response to pressing the trigger, the second flow path is closed and the first flow path is opened by operation of the second relay control, and the first flow path is then closed in response to operation of the third relay control and in response to closure of the normally open switch when the actuating means is in the second position.

5. The welding system of claim 5, wherein the safety circuit further comprises a plug means and means for receiving the plug means to connect the switch with the first flow path.

6. The welding system of claim 6, further comprising a fourth electrical flow path for connecting the first relay control with the trigger when the plug means is disconnected from the means for receiving, the safety circuit being adapted for closing the fourth flow path and maintaining the first, second, and third flow paths in an open state in response to disconnection of the plug means.

7. The system of claim 5 wherein the actuating means comprises an air cylinder mounted to the headband through a bracket and a piston mounted to the hood at a position remote from the air cylinder.

* * * * *

UNITED STATES PATENT AND TRADEMARK OFFICE
CERTIFICATE OF CORRECTION

PATENT NO.  : 5,189,735
DATED       : March 2, 1993
INVENTOR(S) : Peter J. Corona It is certified that error appears in the above-identified patent and that said Letters Patent is hereby corrected as shown below:

```
Column 1, line 13, before "electric" change "or" to
          -- of --.
Column 1, line 55, after "system" change "With" to
          -- with --.

Column 2, line 37, after "28" insert a period.
```

In the Claims

```
Column 4, line 65, change "claim 2" to -- claim 1 --.

Column 5, line 1, change "claim 2" to -- claim 1 --.

Column 6, line 10, change "claim 5" to -- claim 4 --.
Column 6, line 15, change "claim 6" to -- claim 5 --.
Column 6, line 23, change "claim 5" to -- claim 4 --.
```

Signed and Sealed this

Twenty-eighth Day of December, 1993

Attest:

BRUCE LEHMAN

Attesting Officer

Commissioner of Patents and Trademarks